United States Patent [19]

Coleman et al.

[11] Patent Number: 4,759,917
[45] Date of Patent: Jul. 26, 1988

[54] OXIDATIVE DISSOLUTION OF GALLIUM ARSENIDE AND SEPARATION OF GALLIUM FROM ARSENIC

[75] Inventors: James P. Coleman; Bruce F. Monzyk, both of Maryland Heights, Mo.

[73] Assignee: Monsanto Company, St. Louis, Mo.

[21] Appl. No.: 18,110

[22] Filed: Feb. 24, 1987

[51] Int. Cl.$^4$ ................. C01G 15/00; C01F 28/02
[52] U.S. Cl. ..................... 423/87; 423/111; 423/112; 423/115; 423/122; 423/132; 423/617; 423/624; 556/1; 556/37; 260/500 SH; 260/404; 252/183.11
[58] Field of Search ............... 423/87, 111, 112, 115, 423/122, 132, 135, 617, 624; 556/1, 37; 260/500.5 H, 404; 502/167; 252/188.31

[56] References Cited

U.S. PATENT DOCUMENTS

| | | | |
|---|---|---|---|
| 3,224,873 | 12/1965 | Swanson | 75/101 |
| 3,821,351 | 6/1974 | Lucid | 423/54 |
| 3,927,172 | 12/1975 | Stevens | 423/135 |
| 3,971,843 | 7/1976 | Helgorsky et al. | 423/181 |
| 4,094,753 | 6/1978 | Charlton et al. | 423/132 |
| 4,362,560 | 12/1982 | Abrjutin et al. | 75/63 |
| 4,404,174 | 9/1983 | Leveque et al. | 423/112 |
| 4,517,096 | 5/1985 | Sekine et al. | 423/112 |
| 4,587,111 | 5/1986 | Wynn | 423/624 |
| 4,631,177 | 12/1986 | Yotsuyanagi et al. | 423/112 |
| 4,666,575 | 5/1987 | Kubo | 423/87 |

FOREIGN PATENT DOCUMENTS 0245736  5/1984  Japan .................. 423/132

OTHER PUBLICATIONS

Xiang et al., *Acta Metallurgica Sinica*, 18 (2), 221 (1982).

Primary Examiner—Helen M. S. Sneed
Assistant Examiner—Anthony McFarlane
Attorney, Agent, or Firm—Wendell W. Brooks; Arthur E. Hoffman; Arnold H. Cole

[57] ABSTRACT

Gallium is recovered from gallium arsenide by reacting and dissolving the gallium arsenide with an oxidant and a complexing agent, especially with water insoluble hydroxamic acids with mild conditions, e.g. with aqueous hydrogen peroxide and mild temperature, to effect separation of gallium hydroxamic acid chelates from water soluble arsenic compounds.

49 Claims, No Drawings

OXIDATIVE DISSOLUTION OF GALLIUM ARSENIDE AND SEPARATION OF GALLIUM FROM ARSENIC

The present invention relates to the oxidation of gallium arsenide and methods, procedures and compositions involved therein, and is particularly directed to the recovery of gallium from gallium arsenide by a method involving oxidation in the presence of a water insoluble complexing agent, particularly a hydroxamic acid, and separation of the resulting gallium complex from water soluble arsenic compounds.

BACKGROUND OF THE INVENTION

Gallium arsenide, along with derivatives such as gallium aluminum arsenide, is used in a wide range of electronic and optical applications. During the manufacture of gallium arsenide devices, as much as 90% of the gallium arsenide becomes waste. Gallium is not readily available from primary sources, but is produced in relatively small quantities as a byproduct from aluminum, zinc and phosphorus operations. Since gallium is expensive and relatively scarce, gallium arsenide waste represents a valuable source for gallium.

Gallium arsenide is a very stable material and methods for its recovery often involve very stringent means such as vacuum thermal decomposition or treatment with very reactive agents. Thus Abrjutin et al, U.S. Pat. No. 4,362,560, discloses a vacuum-thermal decomposition process for treating various high grade gallium arsenide wastes, and also references various prior art processes, including oxidation of gallium arsenide under anhydrous conditions with chlorine. Abrjutin et al further describe preliminary hydrochemical treatment to remove impurities, involving treatment with an aqueous solution of hydrochloric acid in the presence of an oxidizing agent. Nitric acid or hydrogen peroxide are preferred for use as the oxidizing agent. The plates of gallium arsenide after this hydrothermal treatment are subjected to vacuum-thermal decomposition. Bird et al, Production of High Purity Gallium from Scrap Gallium, SME Minisymposium on "The Hydrometallurgy of The Rarer Metals", Dallas, 1982, pp. 59–64, describes various sources of gallium arsenide scrap, and a process to produce high purity gallium therefrom; the process includes disassociation by leaching in hot aqua regia (4HCl:1 HNO$_3$), and neutralization of the acid solution with NaOH to precipitate Ga(OH)$_3$. The byproduct salt solutions, the acid fumes and NO$_x$ emissions make such systems difficult to deal with from both a health and environmental point of view. The dissolved arsenic and other metal ions (from dopants and co-metals, etc.) cause serious problems in disposal of the reaction mixture. The product solution, which may contain only a percent or so of gallium, must have all of its acid neutralized to recover gallium hydroxide as gallium hydroxide solid. Also the solid is gelatinous and extremely difficult to filter.

There is extensive literature on chemical etching of various semiconductor materials, such as Werner Kern, Chemical Etching of Silicon, Germanium, Gallium Arsenide, and Gallium Phosphide, RCA Review, Vol. 39, June, 1978, pp. 268–309, which in discussing general etching mechanisms of semiconductors, indicates that they typically involve oxidation-reduction reactions, followed by dissolution of the oxidation products, frequently by complexing. In the case of silicon and germanium the oxidation agent is frequently HNO$_3$, and the complexant is HF. NaOH-H$_2$O$_2$ and H$_2$SO$_4$-H$_2$O$_2$-H$_2$O solutions are listed among the most commonly employed etchants for GaAs. The Electrochemistry of Semiconductors, Ed. by P. J. Holmes, Academic Press, London and New York (1962), at pages 367–375, has a section on Etchants for the More Important Semiconductors, and at page 372 lists an NaOH and H$_2$O$_2$ solution and an HCl, HNO$_3$ and H$_2$O solution among those for gallium arsenide. A recipe for chemical polishing Indium Telluride includes Br$_2$ and acetic acid saturated with citric acid. A citric acid-hydrogen peroxide-water system for preferential etching of GaAs is described by Otsubo et al, J. Electrochem. Soc., 125 (5), pp. 676–680.

Some hydroxamic acids have been utilized in the art for extraction purposes. U.S. Pat. No. 3,821,351 issued June 28, 1974 to M. F. Lucid discloses certain N-substituted hydroxamic acids useful as extractants for the recovery of copper, molybdenum, uranium, iron and vanadium. U.S. Pat. No. 3,971,843 issued July 27, 1976 to J. Helgorsky et al discloses a solvent extraction process employing certain substituted hydroxyquinolines for the recovery of gallium from aqueous alkaline solutions.

Xiang et al in Acta Metallurgica Sinica 18 (2), 221, (1982) describe the use of a certain undefined fatty hydroxamic acid for the recovery of gallium from aqueous acid solutions.

Iwaya, Japanese Patent No. SHO60(1985) 245736, Appl. No. Sho. 59(1984)-101504, published Dec. 5, 1985, discloses a method of recovering gallium, using hydroxamic acids, described as having —C(O)NHOH groups, from high-basicity aqueous sodium aluminate solutions.

We have now discovered a process which can be adapted so that GaAs is easily dissolved using mildly reactive reagents, and the gallium and arsenic are separated without the need for use of large amounts of neutralization reagents, and with minimal (theoretically zero) emissions of hazardous chemicals into the environment. The process can avoid harmful NO$_x$ emissions and provide for regeneration of the dissolution reagent for re-use.

SUMMARY OF THE INVENTION

In a preferred aspect, the invention involves effecting disassociation and dissolution of gallium arsenide material with an oxidizing agent and an N-organohydroxamic acid, especially with aqueous media present so that a gallium hydroxamic acid complex can be separated from an aqueous phase which largely retains the arsenic product. The invention further involves use of extraction procedures, with or without the use of organic solvent, to separate gallium complexes from the aqueous phase, and stripping procedures to strip the gallium from the organic phase and to free the hydroxamic acid in the organic phase for re-use in disassociation and dissolution reactions or additional extractions. The invention can also involve adjusting the pH of reaction mixtures, as by addition of alkali or acid, to have appropriate pH ranges to effect good extraction of the gallium and possibly also to effect separation from metal impurities. In a particularly preferred aspect of the invention, hydrogen peroxide is used as the oxidizing agent in order to use a mild oxidizing reagent which is reduced to an environmentally acceptable material. In another aspect the invention involves effecting disassociation and dissolution of gallium arsenide with an oxidizing agent and a polybasic or polyfunctional phosphorus chelating agent. In a further aspect the invention involves oxidizing gallium arsenide in the presence of a complexing agent to effect disassociation and dissolution, and then extracting the gallium from the resulting solution with an organic extractant comprising a water insoluble N-organohydroxamic acid.

In another aspect, the invention involves effecting disassociation and dissolution of gallium arsenide with an oxidizing agent and in contact with a liquid comprising a hydroxamic acid. The invention thus includes use of both N-H and N-organohydroxamic acids. Note that N—H hydroxamic acid means that the H has not been substituted for a functional group such as an alkyl group. Thus, N—H hyroxamic acid is a non-N-substituted hydroxamic acid.

The invention also concerns a mixture having a N-organohydroxamic acid in contact with fine particle GaAs, providing a favorable environment for oxidation of the GaAs. The invention is further concerned with a liquid mixture having an organic phase comprising a hydroxamic acid chelate of gallium, and an aqueous phase comprising arsenic acids.

DETAILED DISCLOSURE

In an exemplary and preferred process of the invention the process comprises blending material containing gallium arsenide (or gallium aluminum arsenide or gallium indium arsenide, etc.) with a liquid N-alkylalkanohydroxamic acid and then adding hydrogen peroxide with stirring. Reaction times may be 5–10 minutes without heating, and less than two minutes with heating. Nearly instantaneous reactions are achievable with adequate heating and stirring. The temperature when heating is employed can be mild, such as 50° to 80° C. or so, or on up to about the boiling point of the aqueous mixture, although it will not generally be desirable to boil away reactants. If desired, higher temperatures can be employed at elevated pressure, in order to accelerate the reaction, but such conditions are not usually necessary.

It is also worthy of emphasis that the exemplary process is adaptable to use with a wide variety of gallium arsenide feed or source materials. Thus the process can be used for relatively pure gallium arsenide scrap, or with materials in which the gallium arsenide is only a small fraction of the content. The hydroxamic acid and hydrogen peroxide can be used to recover gallium and arsenic from scrap containing large amounts of other materials, without undue loss of reagents. By contrast, some more reactive reagents have a greater tendency to react with other components of the scrap with loss of reagent, and to produce large quantities of environmentally objectionable waste from the other components. The present exemplary process gives good separation from arsenic, under mild conditions, and is adaptable to wide range of feeds, including those with a small GaAs content.

Using HA to designate a hydroxamic acid, a $\overline{\phantom{aa}}$ above a compound to designate organic phase solubility and a $\underline{\phantom{aa}}$ below a compound to designate insoluble solids, the main reactions in the exemplary process appear to be:

$$GaAs + 3H_2O_2 + \overline{3HA}/ \rightarrow \overline{GaA_3} + H_3AsO_3 + 3H_2O,$$

or if enough $H_2O_2$ is used to further oxidize the arsenous acid, $$GaAs + 4H_2O_2 + \overline{3HA}/ \rightarrow \overline{GaA_3} + H_3AsO_4 + 4H_2O$$

Since the starting reagents in the exemplary process are of low acidity or bascity (the pKa of hydroxamic acids are about nine and that for hydrogen peroxide is about 12), the reagents are mild. (The pH during the reaction of such agents may be about 0.5 to 1, due to the arsenic and/or arsenous acids produced, but will vary with acids, alkali or other agents used.) The hydrogen peroxide is converted to water and any excess hydrogen peroxide readily decomposes to water and oxygen, both environmentally acceptable materials. The gallium and arsenic are separated when the stirring of the reaction mixture is stopped since $GaA_3$ is oil soluble and water insoluble while $H_3AsO_3$ or $H_3AsO_4$ (or in general their salts) are water soluble. The gallium can be recovered from the hydroxamic acid by stripping procedures as described herein. The arsenic can be recovered by evaporation of water and drying to produce $As_2O_3$ or $As_2O_5$, which are useful products as such, or which can be converted to elemental arsenic. Alternatively, the arsenic can be converted to water insoluble metal arsenate salts such as copper arsenate, calcium arsenate or iron (III) arsenate. These can be useful products in themselves or are easily disposed of in an environmentally acceptable manner due to their very high water insolubility.

The exemplary process involves an immiscible heterogeneous system with solid GaAs particles in contact with two immiscible liquid phases. Aside from whether the oxidation occurs at an interface or in one of the liquid phases, it appears that the mixture having a hydroxamic acid, preferably N-organohydroxamic acid, in liquid contact with the GaAs provides a favorable environment for oxidation of the GaAs. Also the process produces a two-phase liquid mixture in which an organic phase comprises hydroxamic acid, preferably a N-organohydroxamic acid, chelate of gallium, and the aqueous phase comprises one or more acids of arsenic, and the phases can be readily separated to separate the gallium and arsenic. Since the product results from decomposition of GaAs, the gallium chelate and arsenic acids will generally be in equimolar relationship.

The reactions herein can suitably be carried out with stoichiometric amounts of reagents, or say an excess of 10 to 20% or so of oxidizing agent and complexing agent, compared to the gallium arsenide, although a 2 or 3 fold excess or larger can be used if desired. If less than a stoichiometric amount of hydroxamic acid is used, the reaction of GaAs will generally be incomplete, but such amounts can be used when partial reaction is acceptable.

It has been found that a number of complexing and chelating agents are effective in the present invention in aiding the dissolution of gallium from gallium arsenide. Such agents include a number of polycarboxylic acids and their salts, phosphorus acid salts, polyphosphoric acid compounds and hydroxamic acids. Among these, the N-organohydroxamic acids are a particularly useful class of chelating agents for use herein. The N-organohydroxamic acids are very effective in conjunction with oxidizing agents in causing reaction of gallium arsenide with conversion into soluble components. In addition, the N-organo hydroxamic acids can be selected so as to be water insoluble so that the gallium chelated with hydroxamic acid readily separates from aqueous media used in the oxidation of the gallium arsenide, and from the arsenic acids which remain in the aqueous medium. Thus it is particularly advantageous to use N-organo hydroxamic acids which are soluble in organic solvents but insoluble in water. Such substantially water-insoluble hydroxamic acids generally have at least about 8 carbon atoms, and can be represented by the formula $R_1C(O)N(OH)R_2$ in which $R_1$ and $R_2$ are organo groups or $R_1$ is hydrogen, and have a total of at least about 8 carbon atoms and preferably not more than about 40 carbon atoms. $R_1$ and $R_2$ are preferably alkyl groups as in N-alkyl alkanohydroxamic acids, but can contain aromatic, halogen or other groups, provided that the compounds are water insoluble and the groups do not unduly interfere with functionality as extractants for gallium. Exemplifications of $R_1$ and $R_2$ include linear, branched or cycloaliphatic groups although in the case of such cycloalkyl groups as cyclohexyl, care must be taken to have sufficient hydrophobic groups present to provide the desired water insolubility. The hydroxamic acids and their gallium complexes must have appropriate solubility in organic media. The extractants used herein also have high solubility in kerosene and other substantially aliphatic petroleum distillates. $R_2$ frequently represents lower alkyl, particularly of 1 to 3 carbon atoms, or the methyl group. $R_1$ can also have additional N-organo hydroxamic acid groups, as in structures wherein $R_1$ represents $-(CHR_3(CH(R_4)-C(O)N(OH)R_5)$, which are exemplified by di-hyroxamic acids of succinyl compounds; in such compounds at least one of $R_3$ and $R_4$ is an organo radical and the other one be hydrogen, and $R_5$ is an organo radical, and the $R_3$, $R_4$ and $R_5$ organo radicals often have a total carbon number greater than 8 and are preferably alkyl radicals selected from the types of groups described above or illustrated or exemplified herein with regard to $R_1$ and $R_2$. A particular class of useful N-organo hydroxamic acids is represented by the formula $CH_3-(CH_2)_mC(O)N(OH)(CH_2)_nCH_3$ wherein m is an integer from 6 to 16 and n is an integer from 0 to 6. Such N-organo hydroxamic acids, particularly exemplified by N-alkylalkanohydroxamic acids, which are chelating extractants, reversibly extract gallium over a broad range of conditions, as disclosed and described in a commonly assigned co-pending application Ser. No. 937,849 of James P. Coleman, Bruce F. Monzk and Charles R. Graham filed Dec. 4, 1986, the disclosure of which is incorporated herein by reference.

This class of N-organohydroxamic acids, particularly exemplified by N-alkylalkanohydroxamic acids, which are chelating extractants, reversibly extract gallium(III) over a broad range of pH conditions. It happens that gallium(III) exists in aqueous solution in a number of different hydroxide complexes whose relative abundance depends upon pH. The $Ga^{3+}$ salt is the predominant form below pH 2, but its proportion rapidly declines between pH 2 and pH 4, while the fraction of $Ga(OH)^{2+}$ rises to about 50% at pH 3 and then declines to near zero at pH 5; the $Ga(OH)_2$ becomes evident above pH 2, rising to about 65% at pH 4 and then declines to pH 6; $Ga(OH)_3$ becomes evident at pH 3, rising to nearly 60% at a little above pH 5 and then declining to near zero at pH 7; $Ga(OH)_4^-$ appears at about pH 4 and becomes the predominant form over pH 7. Since the tri-hydroxy species $Ga(OH)_3$ is virtually insoluble in water, and is formed in the pH range from about 3 to about 7, a natural limitation is therefore placed on the pH of commercial gallium-containing solutions which do not utilize solubilizing chelating agents.

The N-alkyl alkanohydroxamic acids described herein have been shown to extract gallium(III) from aqueous solution rapidly and selectively in the pH range from about 0.5 to about 12 and to be rapidly stripped of gallium(III) by aqueous solutions with a pH outside this range. This range of pH for gallium (III) extraction coupled with two pH ranges for gallium(III) stripping, namely less than about 0.5 or greater than about 11 or 12, allows the use of these N-alkylalkanohydroxamic acids in a process for gallium (III) extraction from either acidic or alkaline leach solutions and subsequent recovery of the gallium (III) via stripping with either strong acid or strong base. Actually, there is generally some overlap in extraction and stripping conditions, and stripping can be accomplished, for example at pH's of about 11 or 11.5 or above. However, efficiencies are affected, as an extraction, for example, will have low efficiency under conditions where a large proportion of the Ga is partitioned into the aqueous phase. In practicing the present invention, the reaction with gallium arsenide can be conducted in the presence of N-organohydroxamic acid and an aqueous medium, and the pH can subsequently be adjusted prior to separating the phases and the phase separation can be conducted advantageously under the most efficient extraction conditions with those described herein being particularly appropriate. The stripping can be conducted under conditions generally applicable to strip gallium from gallium hydroxamic acid chelates in an organic phase.

When a liquid hydroxamic acid compound is used, it can be used neat as the organic phase in the oxidation-dissolution reaction and the subsequent extraction-separation. However it will often be preferable to use an organic solvent as an extender, or to lower viscosity or lessen absorption or resulting losses of the hydroxamic acid, or to promote phase separation, and the organic phase often includes a liquid hydrocarbon solvent. Such solvent must be substantially water immiscible so as to be separable from the aqueous solutions containing the arsenic values. Suitable solvents include aliphatic and aromatic hydrocarbons such as kerosene, hexane, toluene, methylene chloride, chloroform, carbon tetrachloride, xylene, naphtha, cyclohexane, Chevron Ion Exchange solvent, Kermac 470-B. Solvesso 100 and the like. Kerosene and other low viscosity, high flash point petrolleum distillates are preferred. Generally, the hydroxamic compounds will be present in the organic phase in an amount of at least about 2% by weight. Preferably, the N-alkyl alkanohydroxamic compound will be present in the amount of 2 to 40%, more preferably about 10 to 35%, by weight based on the total organic phase. Viscosity and/or solubility serves to fix the upper limit of the content of said hydroxamic compound which will depend upon the structure of the compound employed. Normally, an amount of above about 20% by weight is employed although amounts as high as 60% can be functional. Certain structures, for example, N-methyl isostearohydroxamic acid, have sufficiently low viscosity that they can be used neat, i.e. without a solvent. Where high complexing salt concentrations, such as phosphates, are present, the extractant efficiency drops off at extractant concentrations less than 10%; while efficient extraction is obtained at even 2 to 5% concentration in the absence of complexing salts. With N-alkyl naphtheno HA's, 20% or so is preferred as higher concentrations tend to have high viscosity.

The organic phase may also contain modifiers which can be a long chain aliphatic alcohol, such as isodecanol or phosphate esters, such as tributylphosphate. Modifiers serve to prevent third phase formation, aid in phase disengagement and/or increase extractant solubility in the hydrocarbon solvent. If a modifier is used, it can be used in amounts of about 0.5% to 50%, or greater, by volume of the hydrocarbon solvent, preferably about 5%. Certain particular types of modifiers, referred to herein as co-extractants, serve to improve the efficiency or speed of the extractions, as further described herein.

In carrying out the extraction part of this invention the gallium bearing aqueous solution is contacted batchwise or continuously with the extractant solvent comprising at least 2% by weight of the N-organohydroxamic acid. The gallium and arsenic values can be separated by simply separating the organic and aqueous phases after the oxidation-dissolution reaction. However, if desired, the degree of extraction and completeness of separation can be improved by additional contacts or extraction stages or other advantageous extraction procedures as described herein. The aqueous feed solution bearing gallium can be adjusted to provide an equilibrium pH in an appropriate range depending upon the particular hydroxamic acid extractant employed and upon the type of leach solution being extracted. The volume ratio of the aqueous phase to the organic phase may be selected to most effectively remove the gallium from the aqueous phase without requiring undue volumes of materials. Aqueous phase to organic phase volume ratios of from 1:20 to 20:1 are believed to be effective, although other ratios may prove effective depending upon the specific characteristics of the solvent extractant and the gallium bearing aqueous solution employed. Phase contact can be achieved using, for example, stirred tanks or mixer-settlers. In the mixer, one phase is dispersed within the other by stirring or some other suitable means of agitation. The extractant forms a complex with the gallium within the organic phase of the two-phase liquid mixture. The dispersion then flows to the settler where phase disengagement occurs under quiescent conditions. Generally, extraction can be carried out at temperatures in the range of 0° C. to 90° C. or more, preferably in the range of about 35° C. to about 70° C. Temperatures of 50°–60° C. are most preferred.

It may be desirable to scrub the galliumloaded organic phase to remove co-extracted metal ions and entrained aqueous phase in order to achieve the desired purity depending on the particular gallium bearing aqueous feed solution employed. This is achieved by washing the gallium loaded solvent with water, aqueous ammonia, dilute acid and/or an aqueous solution of a gallium salt.

The gallium values extracted from the aqueous reaction solution into the organic phase can be stripped from the loaded organic phase without decomposing the hydroxamic acid by contacting one part by volume of it with about 0.5–10 parts by volume, preferably about 0.5–2.0 parts by volume, of an aqueous solution at 0°–80° C., preferably about 15° C.–60° C. The aqueous solution used for stripping the loaded organic phase can be a solution of a mineral acid, caustic or ammonia. Suitable mineral acids include sulfuric, hydrochloric, hydrofluoric, nitric and the like. The preferred mineral acid solution is sulfuric acid containing about 1–400 grams of sulfuric acid per kg. solution, preferably about 100–300 grams per kg. solution. In percentages, this is 1 to 40% sulfuric acid, and preferably 10 to 30%. Suitable aqueous ammonia solutions are solutions containing 50–300 grams ammonia per kilogram of solution, preferably about 100–200 grams per kilogram of solution. Suitable caustic solutions are 5–400 grams NaOH, preferably about 5–80 grams NaOH, per kilogram of solution or 5–500 grams per kilogram solution of KOH, preferably about 5–100 grams per kilogram solution. Phase contact with the stripping solution can be achieved with mixer-settlers, or other suitable devices. In this manner the gallium is recovered from the organic phase into the stripping solution as a gallium salt. The gallium-bearing stripping solution can be treated by conventional means to recover gallium metal, for example, by electrolytic reduction of an aqueous caustic solution of the gallium.

The stripped gallium-free solvent extractant containing hydroxamic acid can be recycled to an extraction circuit for further use in extraction, or for treatment of additional gallium arsenide materials with aqueous oxidants. This ability for recycle appears unique to N-organo hydroxamic acids as substantial decomposition by hydrolysis generally occurs during stripping, particularly under acid conditions, with N-H hydroxamic acid compounds. N—H hydroxamic acids are also oxidized by the oxidizers needed for GaAs dissolution.

While N—H hydroxamic acids have certain disadvantages, as discussed herein, they are useful in the present invention. However, such compounds tend to be solids, and it is necessary to have them in liquid form, as in solution or other liquid phase, in order for them to be significantly effective in the present invention. N—H hydroxamic acids with up to about six carbon atoms are water soluble, although essentially insoluble in aliphatic hydrocarbon solvents. These water soluble hydroxamic acids can be used in combination with an oxidant, e.g. aqueous hydrogen peroxide, to oxidize and dissolve GaAs, recognizing that there will be some losses by oxidation during the GaAs dissolution, and losses by hydrolysis in further procedures. Of course the gallium after an oxidation with aqueous media will be found in the aqueous phase as a hydroxamic acid chelate and will not be separated from the arsenic. Further procedures, as described herein for other water soluble complexing agents, can then be used to separate the gallium. Hydroxamic acids, particularly straight chain hydroxamic acids, with more than about six carbon atoms tend to be water insoluble but can be dissolved in solvents for use herein in combination with oxidants to disassociate and dissolve GaAs. Water immiscible solvents are preferred, as the solvent phase with the gallium chelates can then be readily separated from an aqueous phase which dissolves the arsenic compounds. In general, solvents capable of dissolving the N—H hydroxamic acid can be used. Such solvents include medium polarity solvents such as n-butanol, 2-ethylhexanol, liquid alcohols of 4 to 10 or so carbon atoms, methylene chloride, etc. Also various aromatic hydrocarbon and halohydrocarbon solvents which have been described for use with hydroxamic acids in extraction procedures, e.g. benzene, toluene, xylene, chloroform, etc. Water miscible solvents can also be used, e.g. lower alcohols such as methyl alcohol, ethyl alcohol, acetone, tetrahydrofuran, etc. can be used, but will not provide a separate phase for immediate separation of the gallium from the arsenic. Aliphatic hydrocarbon solvents can be used to whatever extent capable of dissolving the particular N—H hydroxamic acids used, particularly those of branched structure. In the case of polar solvents, there is a potential for oxidative attack by the oxidant on the solvent, and this should be taken into account. In order to minimize solvent degradation, it may be advisable to select oxidatively resistant polar solvents, such as tertiary butyl alcohol or tributyl phosphate, or to keep the oxidation temperature as low as practical.

In the case of highly branched N—H hydroxamic acids which happen to be liquid, the hydroxamic acid can be used in the GaAs oxidation without any solvent, in a manner like the use of liquid N-organohydroxamic acids as described herein. In general the N—H hydroxamic acids when comprised in a liquid can be used in procedures like those described herein for N-organohydroxamic acids, with the water soluble N—H hydroxamic acids giving results similar to the water soluble N-organo hydroxamic acids, and the water insoluble N—H hydroxamic acids giving results similar to those with water insoluble N-organohydroxamic acids. Also the use of water immiscible solvents with water insoluble N—H hydroxamic acids is advantageous in aiding in the separation of the resulting gallium chelates from aqueous reaction media in a manner similar to the advantage with water insoluble N-organohydroxamic acids of such solvents (or the neat N-organohydroxamic acids). Further extraction and stripping procedures to recover and purify gallium can be carried out in general with the N—H hydroxamic acids in accordance with procedures described herein for N-organohydroxamic acids, recognizing that appropriate organic solvents should be selected with sufficient capability to dissolve the N—H hydroxamic acids. Thus in the various uses for hydroxamic acids exemplified with N-alkyl or N-organo hydroxamic acids herein, it is to be recognized that in general N—H hydroxamic acids may be substituted with possibly some modification with respect to solvent use or choice.

Even though the N—H hydroxamic acids can be very effective in combination with oxidants in causing the dissociation and dissolution of GaAs, the use of N-organo hydroxamic acids is strongly preferred because of various advantages including less oxidative degradation, greater hydrolytic stability, lower viscosity and easier strippability of gallium from the chelate.

The extraction and stripping procedures as described herein can also be used in general for removing gallium from aqueous arsenic-containing solutions resulting from oxidizing gallium arsenide in the presence of a water-soluble complexing agent, e.g. sodium tripolyphosphate. Thus gallium arsenide can be treated with an oxidizing agent, e.g. aqueous hydrogen peroxide, and a water-soluble chelating agent, e.g. a polybasic phosphorus compound, to oxidize and dissolve gallium arsenide, and the resulting solution can be contacted with an organic extractant comprising an N-organohydroxamic acid to extract the gallium; the gallium can then be stripped from the organic medium with an acidic or alkaline aqueous liquid, with the hydroxamic acid being removed and remaining in the organic phase.

Methods of preparing the N-alkylalkanohydroxamic acids are known. Such compounds can be prepared by the reaction of a N-alkylhydroxyamine with a carboxylic acid chloride.

The N-organohydroxamic acids used herein can in general be prepared by reaction of N-substituted hydroxylamines with carboxylic acid chlorides. The reaction can be effected by adding the carboxylic acid chloride simultaneously with a base, such as aqueous NaOH, to a solution of the N-alkylhydroxyl amine in organic solvent. The product is purified by thorough water washing to remove by-product salts.

The present invention involves an oxidation of the gallium arsenide. The oxidation raises the arsenic ion to a higher valence state, as from a negative anion to an oxide in which the arsenic has a positive valence, as in $AsO_3^{3-}$ or $AsO_4^{3-}$. The oxidizing agents employed are those capable of effecting the oxidation in the presence of designated complexing agents, preferably in near stoichiometric amounts and in a reasonably short reaction time. Agents which can be employed include peroxide compounds, such as hydrogen peroxide, sodium peroxide, free halogens, e.g. bromine, chlorine or iodine, particularly in the presence of water, aqueous alkali, e.g. sodium hydroxide solutions, nitrogen oxides, e.g. nitric acid. The oxidizing agents can be provided as such, or generated chemically (or electrically) from various sources. Some oxidizing agents which can be used in the present invention, such as nitric acid, are highly corrosive and give off undesirable fumes and produce byproducts which present a disposal problem. In addition, acid agents require large amounts of base for neutralization with attendant costs and disposal problems. There is therefore great advantage in using a mild oxidizing agent, such as aqueous hydrogen peroxide, which does not involve noxious fumes and produces an innocuous byproduct, water. Halogen oxidizing agents require more careful handling than hydrogen peroxide and produce hydrogen halide as a by product, which may be undesirable, depending upon possible use for such product. However when halogen oxidizing agent or even nitric acid are used as oxidizing agents with hydroxamic acids as chelating extractants, it is possible to recover the hydroxamic acid for further use in the process. The recoverability of the hydroxamic acids is in contrast to the fact that a number of other types of agents react or form products in the dissolution which make them difficult to regenerate. It should further be noted that halogens and nitric acid, when used with hydroxamic acids, can be employed in amounts stoichiometrically equivalent to the gallium arsenide, thus providing only relatively small amounts of hydrochloric acid for neutralization or disposal. This contrasts with procedures in which a relatively large amount of aqua regia or similar solution may be employed as a reaction medium.

It is desirable that the N-organo hydroxamic acid have low solubility in water in order to effect ready separation of the chelated gallium from the aqueous oxidizing medium. In Table 1 the aqueous solubilities of a number of hydroxamic acids are reported.

TABLE 1

| AQUEOUS SOLUBILITIES OF N—ALKYLALKANO AND N—H HYDROXAMIC ACIDS | | |
|---|---|---|
| | SOLUBILITY (25° C.) | |
| EXTRACTANT | ppm | molarity |
| versatohydroxamic acid (not N—alkyl) | 1600. | $8.54 \times 10^{-3}$ |
| neotridecanohydroxamic acid (not N—alkyl) | 328. | $1.43 \times 10^{-3}$ |
| N—methyldecanohydroxamic acid | 111./82. | $5/49 \times 10^{-4}$ |
| N—methylhexadecanohydroxamic acid | 1.3 ± 1 | $4.60 \times 10^{-6}$ |
| N—isopropyldecanohydroxamic acid | 3.9 ± 1 | $1.68 \times 10^{-5}$ |
| N—hexyldecanohydroxamic acid | 1.6 ± 1 | $5.71 \times 10^{-6}$ |
| N—(1-nonyldecyl)cyclohexanohydroxamic acid | 0.7 ± 1 | $1.7 \times 10^{-6}$ |
| N—methylnonanohydroxamic acid | 409. | $2.18 \times 10^{-3}$ |

It will be noted that most of the N-alkyl hydroxamic acids have very low solubilities in aqueous media, with the solubility tending to increase with decreasing number of carbon atoms in the hydroxamic acids. The N-methyl nonanohydroxamic acid has relatively high aqueous solubility; however, its solubility in a typical phosphate rock treater dust leachate (containing high concentrations of Al, Zn, Fe, phosphate and other ions) is markedly lower, being 20 ppm ($1.07 \times 10^{-4}$ molarity). This appreciable but limited solubility appears responsible for the effectiveness of N-methylnonanohydroxamic acid in extracting Ga from such leachates, with regard to both rate and extent of the extraction compared to higher carbon number N-alkyl hydroxamic acids. For the extraction to occur, it is necessary that the extractant have some slight solubility in the aqueous Ga-containing medium.

Very little water solubility is a useful characteristic of extractants in general and is useful in the present invention in order to effect separation from the aqueous oxidizing medium. However, the invention apparently involves extraction of the gallium from aqueous media, so it is essential that the extractants have some limited solubility in such media; but it is generally desirable that the hydroxamic acid solubility in the aqueous reaction phase not exceed 300 ppm. The solubility will vary somewhat with the concentration of metal salts in the aqueous medium, because of a salting out effect. In order to improve the solubility of the extractant in an aqueous metal-containing phase, N-alkyl hydroxamic acids can be selected which have a number of carbon atoms toward the lower end of an eight to 20 carbon atom range. Even so, such extractants will have little solubility in water, generally less than 0.1% and be substantially water insoluble.

It is further generally desirable that the water-insoluble extractant have high solubility in organic media, preferably including high solubility in aliphatic hydrocarbons, and the extractants should have a sufficiently high number of carbon atoms to assure such solubility. It is further desirable that the water insoluble extractant have a high solubility ratio with respect to relative solubility in an organic medium used compared to an aqueous medium, as expressed by partition ratios in organic: aqueous of >10:1, and preferably >20:1 and often >100:1.

While it is definitely advantageous to use water-insoluble complexing agents, it is also feasible to use water soluble complexing agents for the oxidation reaction with gallium arsenide, and then rely upon further procedures for separating the complexed gallium from the arsenate ions. The oxidation and formation of gallium complexes has been found to proceed well with a number of complexing agents other than hydroxamic acids. Also, the oxidation proceeds in the presence of short-chain water soluble N-alkyl hydroxamic acids, even with such short chains as N-methyl acetohydroxamic acid, but the chelated gallium does not readily separate from the aqueous oxidation medium.

For efficient extraction of gallium under acid conditions with N-alkylhydroxamic acids, the pH will generally be at least as high as about 1 or 1.2, although varying somewhat with the particular hydroxamic acid used. Also with an effective modifier present, desired results may be obtained at pH's as low as 0.8 or 0.9. With no modifier present, a desirable pH range for efficient removal of Ga from acid solutions having fairly high content of one or more of many of the other metal ions potentially present, is about 1.2 to about 1.6. A pH of 1.2 or above permits efficient removal of Ga, while a pH of 1.6 or lower tends to avoid substantial precipitation of many metal ions. If conditions which cause precipitation are employed, the solutions are more difficult to handle and extra filtrations may be required. If substantial quantities of other metal ions are not present, acid pH's above 1.6 may be employed for the extraction without difficulty. In the recovery of gallium arsenide materials, the metal impurities are often in very minute amount and it can be advantageous to use relatively high pH for the extraction of gallium, such as above 1.8 and preferably in the range of about 1.8 to about 2 or 2.5. The use of these or higher pH ranges makes it possible to obtain nearly complete gallium separation in a single contact, such as just separating the organic and aqueous phases following an oxidation-dissolution reaction. The small quantities of dopants or metal impurities frequently present will not ordinarily cause a precipitation problem. Then, if desired, such metal impurities as are extracted can be removed from the solutions containing the chelated gallium by washing with dilute acid solution, such as a 1% sulfuric acid solution. Such impurities as indium, tin, lead, zinc and aluminum may be removed by such procedures.

After the gallium has been extracted into organic media with a water insoluble N-organo hydroxamic acid, it may be stripped from the organic medium with an acidic aqueous solution, preferably of pH no greater than 0.5 for efficient extraction, although stripping to some extent can be effected at higher pH's, using high stripping solution volumes or repeated contacts with fresh solution to achieve the desired degree of extraction.

For operation under alkaline conditions, one can adjust the pH of the solution to pH above 7 following the oxidation-dissolution reaction with gallium arsenide and then separate the organic hydroxamic phase containing the gallium from the aqueous phase. An efficient extraction and recovery process can extract Ga with N-organo hydroxamic acid at pH of about 7 to 11 and recover the Ga from the extractant by stripping with aqueous alkaline medium at pH of about 11 to about 12 or above, particularly at about 11.5 to 12. There is some overlap in extraction and stripping ranges and some extraction is obtainable in pH ranges up to about 12 or so, but extraction is more efficient at pH's near 11 or lower. However marginal results can be improved by using higher concentrations of hydroxamic acids, and the ranges may vary somewhat with the particular hydroxamic acid or conditions.

Among the various hydroxamic acids useful in the present invention are, for example, N-methylnonanohydroxamic acid, N-methyl-naphthenohydroxamic acid, N-methyl 2-hexyl-decanohydroxamic acid, N-methyl stearo-hydroxamic acid, N-methyl isostearohydroxamic acid, N-methyl neotridecanohydroxamic acid, N-isopropyl decanohydroxamic acid, N-hexyldecanohydroxamic acid, N-(1-nonyldecyl) cyclohexanohydroxamic acid, N-ethyl naphthenohydroxamic acid, N-methyl neodecanohydroxamic acid, N-phenyl naphthenohydroxamic acid, N-methyl 4-decylbenzoydroxamic acid, N-n-propyl naphthenohydroxamic acid, N,N'-dimethyl n-decylsuccinodihydroxamic acid. Efficiencies of the hydroxamic acid will vary somewhat, and the more water insoluble hydroxamic acids will separate more readily from aqueous reaction product. However, those hydroxamic acids which are slightly water soluble, or even considerably water soluble, can be separated from aqueous media by organic solvent extraction if necessary if they have some oil solubility, as will be the case, for example, for N-methyl pentanohydroxamic acid. In addition, highly water soluble hydroxamic acids can be used in the oxidation reaction, e.g. N-methyl acetohydroxamic acid, but special provisions will be needed, as discussed herein, to separate the resulting Ga ions from aqueous media.

Various N-H hydroxamic acids are suitable for use herein and representative compounds may have a total of up to about 30 or so carbon atoms, with those of about 7 or more carbon atoms being water insoluble. Examples of suitable N-H hydroxamic acids include naphthenohydroxamic acid, nonanohydroxamic acid, decanohydroxamic acid, stearohydroxamic acid, neo-tridecanohydroxamic acid and modifications of the various N-organo hydroxamic acids disclosed herein, but with the N-alkyl or other N-organo group replaced by a hydrogen substituent. Similarly, in the representative formulae for hydroxamic acids disclosed herein, the N-organo substituent can be replaced by a hydrogen substituent, as in $R_1C(O)N(OH)R_2$ in which $R_2$ becomes hydrogen, and R has at least about 8 carbon atoms for water insoluble hydroxamic acids.

Among other complexing agents useful in the oxidation of gallium arsenide are certain salts and acids of phosphorus. Suitable phosphorus compounds in general are chelating agents by virtue of having two or more phosphorus acid moieties, or by having three hydrogens in a phosphorus acid replaced by metal anions, as in alkali metal triphosphates. Some other salts of dibasic or polybasic acids are similarly effective in the reaction, for example, sodium oxalate. The acids, generally polycarboxylic acids, can be used in acid form, but the alkali metal salts are generally more water soluble and convenient for use. Phosphorus salts and similar complexing agents generally produce water soluble gallium complexes which do not ordinarily separate from an aqueous oxidizing medium. The recovery of the gallium values then requires a separate step, such as a solvent extraction with hydroxamic acid extractants, or other strong metal extractants, such as Kelex ® 100, utilizing procedures as described herein and as further described in aforesaid copending application Ser. No. 937,849, the disclosure of which is incorporated herein by reference. Because of the additional step involved when water-soluble complexing agents are used, it will ordinarily be preferable to use water-insoluble N-organohydroxamic acid complexing agents. However, in some special circumstances it may be desirable to utilize complexing agents other than water-insoluble N-organohydroxamic acids, and then use solvent extraction or another procedure to recover gallium values. Also it is possible to utilize neutralization or other pH regulation procedures to recover gallium hydroxide by filtration, but such procedures have a number of undesirable aspects. In some particular instances with soluble complexing agents, an insoluble gallium complex may form and precipitate from the aqueous oxidizing medium, as is the case when ethylene diphosphonic acid is employed. In such cases, the precipitate can be conveniently separated from the aqueous medium by filtration or decantation, and this provides a convenient separation of the gallium and arsenic values.

It can be theorized that water soluble hydroxamic acids might be present in higher concentration at the oxidation site of an aqueous oxidant, but the water insoluble N-organohydroxamic acids seem to be very effective in providing conditions for oxidation of gallium arsenide. However it is feasible to use an N-organohydroxamic acid of limited hydrophobic character, such as having a total of 5 to 7 carbon atoms and limited water solubility but still with good oil or organic solubility. After such compounds are used in an oxidation to form a chelate with gallium, the chelate can be extracted into organic media by contacting the reaction product solution with high volumes of hydrocarbon solvent, compared to the volume of reaction product solution.

The phosphorus complexing agents useful herein are characterized by being polybasic phosphates, preferably tribasic phosphates; or polyphosphonates having two or more phosphonate groups and chelating ability, i.e.

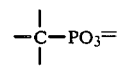

groups in which the groups can be salts or acids, especially alkali metal salts; and include for example, tribasic sodium orthophosphate, $Na_3PO_4$, tribasic potassium orthophosphate, $K_3PO_4$, sodium pyrophosphate, $Na_2PO_3$-O-$PO_3Na_2$, sodium tripolyphosphate, $Na_5P_3O_{10}$, ethylene diphosphonio acid, $H_2PO_3CH_2CH_2PO_3H_2$, and certain Dequest ® brand name water treatment compounds marketed by Monsanto, including

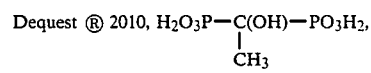

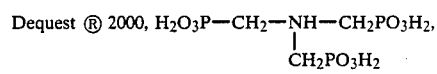

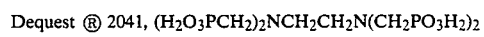

and

Dequest ® 2061,

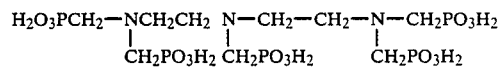

The Dequest ® water treatment compounds can be used in either acid or partial or complete metal salt forms. Of the Dequest ® compounds, Dequest ® 2010 works well, while the other named Dequest ® compounds result in gallium arsenide dissolution, but at a rather slow rate and with some degradation of the compounds, possibly by oxidation. A dibasic sodium phosphate, $Na_2HPO_4$ also was effective in causing dissolution, but at a slow rate and with some white precipitate formation.

The present invention will be useful for recovering gallium from various sources of gallium arsenide, whether substantially pure gallium arsenide, gallium aluminum arsenide, gallium indium arsenide, or gallium arsenide contaminated with various metal or other impurities or dopants. Such possible sources include, for example, those described in the above-referenced Bird et al publication, being waste or scrap materials generated during gallium arsenide wafer manufacture and processing into semiconductor devices, and described as endcuts, broken wafers, saw kerf, lapping compound, etc., and the waste can contain Fe, Al, Si, Zn, and other metallic and nonmetallic wastes listed in the publication. While the emphasis in the present application is on separation of gallium from arsenic, the invention can also involve separation of gallium from other metals and further purification of gallium. In particular, water insoluble N-alkyl hydroxamic acids are selective extracting agents and the process can be adapted to effect separation of gallium from many metals, particularly by appropriate adjustment of pH; or wash solutions can be used to remove metel impurities from solutions containing gallium hydroxamate chelates. At relatively low pH, many of the metals are water soluble, while the gallium hydroxamic acid chelate is extracted into organic media. If desired the oxidation, dissolution, extraction and washing procedures herein can be adapted to produce very high purity gallium. Also alternatively the gallium obtained in the present invention can be subjected to further chemical or physical treatments for further purification such as electrolytic deposition, vacuum-thermal deposition, chemical dissolution, extraction, filtration, including for example various procedures as disclosed in the above-referred to Production of High Purity Gallium from Scrap Gallium and Abrjutin et al U.S. Pat. No. 4,362,560.

Some sources of gallium arsenide contain only small amounts of gallium arsenide such as 1 or 2% by weight, and the exemplary process herein using hydrogen peroxide and N-organo hydroxamic acid is specially useful for recovery from scrap material containing only small amounts of gallium arsenide.

The present invention is especially concerned with the recovery of gallium from gallium arsenide. However, since the disclosed reagent systems result in disassociation and dissolution of gallium arsenide, they can also be used for etching and polishing etc. of gallium arsenide and the application of novel reagent systems herein to such use is included in the invention. In particular, a combination of hydrogen peroxide and N-alkylhydroxamic acid may find valuable use as a mild system for etching or polishing gallium arsenide.

The extent of hydrolysis of some hydroxamic acids used in some gallium extraction, washing and stripping procedures was determined by spectrophotographic analysis of the solution after completion of the procedures, with results as reported in Table 2.

TABLE 2

| Extractant | % Decomposition |
|---|---|
| N—H naphthenohydroxamic acid | 45.0% |
| N—Methyl naphthenohydroxamic acid | +0.14% |
| N—Ethyl naphthenohydroxamic acid | −0.53% |
| N—Propyl naphthenohydroxamic acid | +0.74% |

The results show that the unsubstituted hydroxamic acid had a very high decomposition, 45%, while the N-alkyl substituted hydroxamic acids had very little decomposition, with the minor variances from zero decomposition (above or below) being within the range of error of the analysis. The procedures and further information on the hydrolytic stability of N-alkyl hydroxamic acids are reported in the aforesaid copending application Ser. No. 937,849. The hydrolytic stability of the N-alkyl hydroxamic acids is an advantage for their use in the present invention.

The N-organo substituted hydroxamic acids used herein have various advantages as extractants over prominent commercially available or developmental extractants, many of which have limited applications which do not include gallium extraction. While consideration of more than a half-dozen of such types of previously known agents indicates that some of them possess a fair number of the following listed properties, none of them possess all of the desired properties, and even the previously known N-H hydroxamic acids are lacking in some of the desired properties. The desirable properties of the N-alkyl hydroxamic acids include high solubility not only in aromatic solvents, but also in kerosene and other aliphatic solvents, thereby avoiding the need for generally more costly aromatic solvents; low aqueous solubility; high hydrolytic stability; and high stability constant; selectivity with respect to metals; wide operating pH range including utility of both acid and basic stripping agents; fast strip kinetics; high metal loading; weak acid character; chelating mechanism; labile complexes with normally substitution-inert metals; reversible Co extraction; environmental compatibility and low toxicity; performance modification by structure modification; relatively low cost; lack of acid or ammonia loading; lack of surfactant properties, including lack of such properties of potential hydrolysis products of particular classes; no anion carry over; no interference from $Ca^{2+}$ ion; and no need to use hydrochloric acid.

EXAMPLE 1

Gallium was recovered from Lap Sludge by simultaneous dissolution and separation. The Lap Sludge was a residue of a powdered aluminum oxide polishing compound used to polish gallium arsenide wafers and contained small amounts of gallium arsenide, analyzing as 17.7 mg Ga/gram and 13.4 mg As/gram. A 20.03 gram amount of the Lap Sludge was placed in a 500 ml flask along with 42.4 grams of N-methyl nonanohydroxamic acid (85.4% purity) and 50 ml of aliphatic hydrocarbon solvent (Kermac 470B petroleum distillate). A 64.2 gram amount of 30% aqueous $H_2O_2$ was added in three equal portions at 10 minute intervals, with stirring and slight warming. The reaction appeared complete (by loss of black GaAs color) after the second addition. The pH was raised by addition of a 50 ml amount of 29% aqueous ammonia solution, with stirring. Some gas evolution, due to excess hydrogen peroxide, occurred and was allowed to go to completion. The liquids were decanted into a separatory funnel and the organic and aqueous phases were separated. The organic phase was washed three times with 200 ml portions of water. Neither arsenic nor gallium was detectable in the washings (detection limit less than 1 ppm for each element). The organic phase was mixed with a 150 ml portion of 30% $H_2SO_4$ for one hour and the phases which then formed were separated. The treatment of the organic phase was repeated with an additional 150 ml of 30% $H_2SO_4$, and the aqueous acid stripping solutions were combined and found to contain 1100 ppm Ga and only 15 ppm As. This represents 17.8 mg Ga per gram of starting sludge, indicating complete dissolution and separation of the Ga in the starting sludge.

The solids, from which the liquids from the reaction mixture had been decanted, were slurried with 150 ml of 5% nitric acid and then filtered, and the solids were then washed successively with water, ethanol and acetone, and air dried to a weight of 18.05 grams. The dilute nitric acid and other wash solutions were combined with the aqueous phase which had been separated from the organic phase after the reaction, and the resulting solution was found to have 2510 ppm As and only 114 ppm Ga. This represents 17.3 mg As/gram of starting sludge, or more than the starting concentration, indicating good dissolution and recovery of the arsenic. (It is noted that the analysis of arsenic in the starting material may have been low, as it would presumably be equal to gallium on an atomic basis, and only slightly below on relative atomic weights; and there was good agreement between starting and recovered gallium.) In fact this result suggests that the procedure of the invention may be more effective in recovering the arsenic from Lap Sludge than the aqua regia procedure used for the base analysis.

In the above procedure, ammonia was used to adjust the pH prior to separating the organic and aqueous phases. This was to enhance the extraction of the gallium hydroxamic acid complex into the organic phase. Such extraction is generally improved by raising the pH to about 1 to 1.2 or higher. Other alkaline materials can be used for such pH adjustment, for example sodium hydroxide, potassium hydroxide or other caustic materials. The treatment of the solids in the above procedure with dilute nitric acid was done as a precaution for possible improvement of solubility of salts of metal impurities, including arsenate salts for analytical purposes but may be omitted in a production process.

In the above procedure the gallium was stripped from the organic medium into a sulfuric acid solution. The gallium can be recovered from the sulfuric acid by various procedures, for example by conversion to a caustic solution for electrolytic reduction and recovery of the gallium. In the above procedure, the gallium recovery was very good. However in cases where the gallium extraction in the initial separation is not complete, the aqueous phase can be subjected to further extraction treatment, using for example about an equal volume of hydrocarbon solvent containing 2 to 40% or so by weight of hydroxamic acid extractant, say 20%, and organic extracts can be combined for stripping. Stripping can be accomplished with, for example, about equal volumes of sulfuric acid, of concentrations, preferably in the range of about 10 to about 30%, say 30%. After the stripping procedure, the hydrocarbon medium which now contains free hydroxamic acid extractant can be recycled for use in the oxidation-dissolution reaction, or for use in extraction procedures on solutions produced directly or indirectly from the oxidation-dissolution reaction.

EXAMPLE 2

A series of procedures were conducted to test effectiveness of various complexing agents with hydrogen peroxide to oxidize and effect dissolution of gallium arsenide. A 0.5 gram amount of GaAs powder was added to a 50 ml beaker with 20 ml deionized water. The complexing agent was added with stirring, followed by addition of 5 ml 30% hydrogen peroxide in water with stirring. Stirring was continued for about 10 minutes with gradual heating on a hot plate to 85° C., with observation for reaction. The mixtures were then allowed to stand at room temperature for about four days with observation for further changes, and the percentage of the starting gallium which had dissolved was determined by analysis of the liquid by atomic absorption. Results are reported in Table 3.

TABLE 3

| Test | Complexing Agent Compound | Amount | Initial Result | % Ga in Solution After 4 Days |
|---|---|---|---|---|
| A | N—methylnonanohydroxamic acid | 3.0 ml | Complete Reaction in 8'30" | 100 |
| B | PC-88A $(CH_3(CH_2)_3CHCH_2)_2P(O)OH$ $\quad\quad\quad\quad\quad\quad\;\;\mid$ $\quad\quad\quad\quad\quad\quad\;\;Et$ | 3.0 ml | No reaction 10 minutes | 13.6 |
| C | Kelex ® 100 | 3.0 ml | Solids formation | 0 |
| D | 4-nonylphenol | 3.0 ml | No reaction, 11 minutes | 0 |
| E | LIX ®-65N | 3.0 ml | No reaction 13 minutes | 0 |
| F | SME-529 | 3.0 ml | No reaction, 10 minutes | 0 |
| G | Acorga P-5100 | 3.0 ml | No reaction, 10 minutes | 0 |
| H | Naphthenic Acid | 3.0 ml | No reaction 10 minutes | 0 |
| I | Di-(2-ethylhexyl) phosphoric acid | 3.0 ml | No reaction 10 minutes | 0 |
| J | Oxine (8-hydroxy quinoline) | 3.02 grams | Precipitate | — |
| K | Ethylene diamine tetracetic acid | 2.98 grams | Little reaction | 84.2 |
| L | Dequest ® 2010 (60% Active) | 3.0 ml | Complete reactor, 1 min, 3 secs. | 100 |
| M | Dequest ® 2041 | 3.0 grams | No reaction, 10 min, or 24 hours | 33 |

TABLE 3-continued

| Test | Complexing Agent Compound | Amount | Initial Result | % Ga in Solution After 4 Days |
|---|---|---|---|---|
| N | CH$_3$(CH$_2$)$_{10}$C(O)NHOH | 3.04 grams | No reaction, 11.5 min. Addn. of 2.98 grams N—methyl-naphtheno HA caused complete dissolution in 60 secs. | — |
| O | Poly(acrylamide HA), water sol. pol, —C(O)NHOH groups | 4.43 grams | GaAs suspended, no reaction | 0 |
| P | H$_2$O$_3$PCH$_2$CH$_2$PO$_3$H$_2$ | 3.28 grams | complete reaction, 3 min., white prec. | 100 in prec. |
| Q | Sodium Tartrate | 3.30 grams | No reaction, 14 min. | 100 |
| R | Sodium Triphosphate | 3.00 grams | Complete reaction, 3 min., 30 secs. | 100 |
| S | Monobasic sodium phosphate (NaH$_2$PO$_4$) | 3.00 grams | No reaction, 17.5 min. | 0 |
| T | Sodium citrate (10% sol., 20 ml H$_2$O omitted) | 30 ml | A little reaction 6 min. 41 sec. complete 11 min., 30 sec. | 100 |
| U | Sodium pyrophosphate Na$_4$P$_2$O$_7$ | 3.01 grams | Complete reaction, 3 min., white prec. | 100 |
| V | Potassium phosphate (K$_3$PO$_4$) | 3.13 grams | Complete reaction, 50 secs. | 100 |
| W | NaH$_2$PO$_4$.H$_2$O (re-test of S) | 3.06 grams | No reaction 40 min. | 0 |
| X | Disbasic Sodium phosphate (Na$_2$HPO$_4$) | 3.10 grams | Slow dissolution white prec., incomplete, 25 min. | 100 |
| Y | Sodium oxalate | 3.05 grams | Complete reaction, 60 secs.; small prec. | 100 |
| Z | Sodium nitrilo triacetate | 3.0 grams | Complete reaction in 3 min. | 100 |
| α | 1. KOH, 1M | 2.0 ml | No reaction, 10 min. | — |
|  | 2. NaOH, 10M | 1.0 ml | Complete reaction, few secs. of addn. NaOH to hot solution | 100 |
| β | Acetohydroxamic Acid (omitted heating) | 3.0 grams | Complete dissolution in 25 min. Clear colorless solution | 100 |
| γ | N—methyl acetohydroxamic acid (omitted heating) | 3.0 grams | Complete dissolution in 5 min. | 100 |
| ε | dodecanohydroxamic acid with 10 ml 2-ethyl hexanol (omitted heating) | 3.0 grams | Some reaction in 15 min. (mild exotherm). Complete reaction in 6 hrs. | 100 |
| σ | acetohyroxamic acid (omitted heating) | 0.62 grams | 80% reacted in 30 min. | 100 |
| δ | N—methyl acetohydroxamic acid (omitted heating) | 0.80 grams | 90% reacted in 10 min. | 100 |
| ω | octanohydroxamic acid (omitted heating) | 1.48 grams | 52.5% dissolved in 24 hrs. | 100 after addn. of 10 ml n-BuOH |

In most of the tests, the amount reported in solution concerns a single aqueous phase, but when there was a Kelex-100 in the above table is a trade designation for a pheolic compound, which was the 1976 or earlier version of formula:

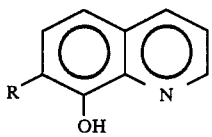

in which R represents:

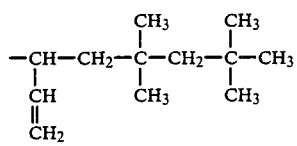

SME-529 is Shell Metal Extractant 529, a hydroxyoxime type solvent extraction reagent for copper, based on a group of hydroxyoximes developed in the Shell laboratories in Amsterdam in which the active component is 2-hydroxy-5-t-nonylacetophenone oxime.

LIX® 65N Reagent is a water insoluble substituted oxime which forms water insoluble complexes with metallic cations, 2-hydroxy-5-nonylphenyl, phenylketoxime.

Acorga P-5100 is a formulated chemical containing 5-nonyl salicylaldoxime and nonylphenol, with a low level of kerosene.

It can be seen from Table 3 that with $H_2O_2$ under mild conditions, N-methyl nonanohydroxamic acid was an effective complexing agent (Test A), with reaction and dissolution of the GaAs occurring in a relatively short time, while reaction under the test conditions did not occur with a number of known complexing agents but did with several others. However agents such as sodium citrate are water soluble and do not result in immediate separation of the gallium and arsenic products. It is of interest that reaction did not occur with an N—H hydroxamic acid, dodecanohydroxamic acid (Test N) but that addition of an N-alkyl hydroxamic acid, N-methyl naphthenohydroxamic acid, to the test solution resulted in rapid reaction and dissolution of the gallium arsenide. Dodecanohydroxamic acid was successfully employed with a solvent (Test ε), with about 6 hours for complete reaction. A number of compounds with phosphate moieties were useful and reaction of the gallium arsenide occurred. Also, the salts of the various polycarboxylic acids exhibited varying degrees of effectiveness. In the test with polymeric material (Test O) the polymer used may not have been that specified, and in principle the specified polymer should give positive results in view of the positive results with related materials.

The gallium complexed with various watersoluble agents, produced in some of the above tests, can be extracted by use of a hydroxamic acid. The rate of gallium transfer from the water-soluble agent to the hydroxamic acid will depend on the water-soluble agent employed. The higher the denticity of the water-soluble agent, the slower will be the rate of gallium transfer to the hydroxamic acid. For example, the aqueous solution obtained in Test R using sodium triphosphate can be extracted with about an equal volume of hydrocarbon solvent containing 2 to 40% of hydroxamic acid extractant, say 20% N-methyl nonanohydroxamic acid, extracting the gallium and leaving the arsenic acids in the aqueous phase. The gallium and hydroxamic acid can then be recovered by stripping, as described in the discussion of Example 1 above.

EXAMPLE 3

Using the procedure of Example 2, with generally slightly over 3 grams Dequest® 2010 (59.6% active) as complexing agent, a number of different oxidizing agents were employed with gallium arsenide with results as reported in Table 4.

TABLE 4

| TEST | OXIDIZING AGENT | | INITIAL RESULT | % Ga In Solution After 4 Days |
|------|----------|--------|--------|--------|
| | Compound | Amount | | |
| AA | ACl-60 | 3.03 grams | No reaction, 13 min. | 60.2 |
| BB | liquid bromine | 3.0 ml | complete reaction before 5 minutes | 100 |
| CC | 5% NaOCl in water | 130 ml (omitted 20 ml $H_2O$) | No reaction, 10 min; Cl tended to boil off | 0 |
| DD | $Cl_2$ gas | Kept solution saturated for 1 hour | Reaction steady and appeared proportioned to stirring rate. Complete <10 min. with vigorous stirring. | 100 |
| EE | Ozone | Sparged at 0.8 m mole/min. | No reaction in 17 min at room temp. or 10 min with heat; or 15 min in methanol with heat. | — |

It can be seen from Table 4 that halogen oxdiants were effective in general. While AC1-60 did not appear to react, analysis indicated 60.2% of the gallium dissolved. The failure of the NaOCl (Test CC) to show positive results in this test is probably a concentration effect, as chlorine was produced and given off and chlorine was found to be effective in Test DD. Higher concentrations of NaOCl are likely to be effective.

EXAMPLE 4

Using the procedure of Example 2 and 3.0 ml of N-methylnonanohydroxamic acid as complexing agent, a number of oxidizing agents were employed with gallium arsenide, with results as reported in Table 5.

TABLE 5

| TEST | OXIDIZING AGENT | | RESULT |
| --- | --- | --- | --- |
| | Compound | Amount | |
| FF | Potassium persulfate | 3.02 grams | No reaction, 10 min. |
| GG | Iodine | 3.41 grams | complete dissolution of solids |
| HH | HNO₃ conc. | 5.0 ml | complete reaction, 50 secs. |
| II | HNO₃ conc. but no complexing agent | 5.0 ml | complete reaction, 20 min. |
| JJ | Bromine | ~3.4 grams | complete reaction, 37 secs. no heating |
| KK | Iodine | ~3.4 grams | complete reaction, 60 secs. no heating |

A number of the oxidizing agents in Table 5 were effective and gave short reaction times. The contribution of a good complexing agent can be seen by coparing the 50 second reaction with nitric acid and an N-alkyl hydroxamic acid (Test HH) with the 20 minute reaction with nitric acid in the absence of a complexing agent. It should be noted that the 5 ml of concentrated nitric acid has been diluted by the 20 ml of deionized water used in the procedure.

EXAMPLE 5

Oxidation of gallium arsenide with bromine in the absence of water was carried out both with, and without an N-alkyl hydroxamic acid. An approximately 0.5 gram amount of finely divided GaAs was used and the components were mixed and heated as in Example 2. The hydroxamic acid was N-methyl nonanohydroxamic acid. Results are reported in Table 6.

TABLE 6

| Amt. HA | Amt Br₂ | Result |
| --- | --- | --- |
| 3.05 grams | 3.50 grams | Vigorous reaction, complete GaAs solution; no sparks or ignition |
| None | 1.0 ml | The GaAs ignited and burned with sparks and incandescence |

With the vigorous oxidation agent Br₂, the oxidation occurred without a complexing agent. The dissolved the gallium product and the gallium and arsenic can be separated by addition of water to provide two phases.

We claim:

1. The method of dissociating gallium arsenide into a gallium-containing component and an arsenic-containing component which comprises contacting the gallium arsenide with an oxidizing agent and a liquid comprising hydroxamic acid to convert the gallium to a gallium-hydroxamic acid complex and to oxidize the arsenic to a positive valence state.

2. The method of claim 1 wherein the hydroxamic acid is an N-organohydroxamic acid.

3. The method of claim 1 wherein the hydroxamic acid is an N-alkyl hydroxamic acid.

4. The method of claim 1 wherein the hydroxamic acid is an N-alkylalkanohydroxamic acid.

5. The method of claim 1 wherein the liquid comprises a water insoluble N-alkyl hydroxamic acid and water.

6. The method of claim 1 wherein the oxidizing agent is selected from the group consisting of chlorine, bromine, iodine, nitric acid and peroxides.

7. The method of claim 1 wherein the oxidizing agent is aqueous hydrogen peroxide.

8. The method of recovering gallium from gallium arsenide which comprises reacting the gallium arsenide with an oxidizing agent selected from the group consisting of peroxides, chlorine, iodine, bromine, oxyhalides and nitric acid in the presence of a liquid comprising hydroxamic acid to form a gallium-hydroxamic acid complex.

9. The method of claim 8 wherein the hydroxamic acid is an N-organo-hydroxamic acid and a gallium-N-organohydroxamic acid complex is formed.

10. The method of claim 8 wherein the oxidizing agent is hydrogen peroxide.

11. The method of recovering gallium from gallium arsenide which comprises oxidizing the gallium arsenide with an oxidizing agent in the presence of a liquid comprising hydroxamic acid to convert the arsenide to an oxide of arsenic and to form a gallium-hydroxamic acid complex.

12. The method of claim 11 wherein the hydroxamic acid is an N-organo hydroxamic acid.

13. The method of claim 11 wherein the hydroxamic acid is in solution in a solvent.

14. The method of claim 11 wherein the oxidation is conducted in an aqueous medium in the presence of a water insoluble hydroxamic acid and the resulting gallium-hydroxamic acid complex is separated from the aqueous medium and arsenic compounds remaining the aqueous medium.

15. The method of claim 14 wherein the hydroxamic acid is in solution in a water immiscible solvent.

16. The method of claim 15 wherein the hydroxamic acid is an N-organohydroxamic acid and the water immiscible solvent is a hydrocarbon solvent.

17. The method of claim 15 wherein the hydroxamic acid is a non-N-substituted hydroxamic acid and the water immiscible solvent as a polarity sufficient to dissolve the non-N-substituted hydroxamic acid.

18. The method of claim 14 wherein the gallium is stripped from the gallium-hydroxamic acid complex by treating the complex with acid and separating the gallium from the hydroxamic acid which is recovered for recycle.

19. The method of claim 14 in which the gallium is stripped from the gallium-hydroxamic acid complex at a pH either no greater than 0.5 or above 11.

20. The method of claim 11 wherein the oxidizing agent is hydrogen peroxide.

21. The method of claim 20 wherein gallium is recovered from a finely divided scrap material containing only 1% to 2% by weight of gallium arsenide.

22. The method of claim 11 wherein the hydroxamic acid is an N-alkyl hydroxamic acid.

23. The method of claim 11 wherein the hydroxamic acid is represented by the formula $CH_3(CH_2)_mC(O)N(OH)(CH_2)_nCH_3$ wherein m is integer from 6 to 16 and n is an integer from 0 to 6.

24. The method of claim 11 wherein the hydroxamic acid is an N-alkyl alkanohydroxamic acid having up to 3 carbon atoms in the N-alkyl group and a total of about 8 to about 40 carbon atoms in said acid.

25. The method of claim 11 wherein the hydroxamic acid is N-methyl nonanohydroxamic acid.

26. The method of claim 11 wherein the oxidizing agent is nitric acid.

27. The method of claim 11 wherein the oxidizing agent is bromine, chlorine, or iodine.

28. The method of claim 11 wherein the hydroxamic acid is N-methyl naphtheno-hydroxamic acid.

29. The method of claim 14 wherein the gallium-hydroxamic acid complex is separated from the aqueous medium at a pH above about 1.2.

30. The method of claim 14 wherein the gallium-hydroxamic acid complex is separated from the aqueous medium at a pH in the range of about 1.8 to about 2.5.

31. The method of recovering gallium from gallium arsenide which comprises oxidizing the gallium arsenide with an oxidizing agent in a liquid medium comprising an aqueous phase and an organic solvent phase containing a water insoluble N-organohydroxamic acid to obtain a gallium-N-organohydroxamic acid complex and to produce acids or arsenic selected from the group consisting of arsenous acid, arsenic acid, and mixtures thereof, separating the organic solvent phase containing the gallium-N-organohydroxamic acid complex from the aqueous phase containing the acids of arsenic, and mixing the separated organic solvent phase with an aqueous acid to strip gallium from the gallium-N-organohydroxamic acid complex wherein the stripped gallium is transferred from the organic solvent phase to the aqueous acid.

32. The method of claim 31 wherein the oxidizing agent is hydrogen peroxide and the hydroxamic acid is represented by the formula $CH_3(CH_2)_mC(O)N(OH)CH_2)_nCH_3$ wherein m is an integer from 6 to 16 and n is an integer from 0 to 6.

33. A composition comprising a hydroxamic acid in intimate contact with particulate gallium arsenide.

34. The composition of claim 33 wherein the hydroxamic acid is represented by the formula $CH_3(CH_2)_mC(O)N(OH)(CH_2)_nCH_3$ wherein m is an integer from 6 to 16 and n is an integer from 0 to 6.

35. A composition which comprises an organic phase comprising a gallium-hydroxamic acid chelate and an aqueous phase comprising acids of arsenic selected from the group consisting of arsenous acid, arsenic acid, and mixtures thereof or their salt derivatives.

36. The composition of claim 35 wherein the hydroxamic acid of the gallium-hydroxamic acid chelate is an N-organo hydroxamic acid.

37. The composition of claim 36 wherein gallium and arsenic are present in substantially equimolar amounts.

38. The composition of claim 36 wherein the organic phase comprises a hydrocarbon solvent.

39. The method of separating gallium from arsenic in a reaction product mixture resulting from the oxidation of gallium arsenide with an oxidizing agent in the presence of water and a water insoluble N-organohydroxamic acid, which method comprises separating a water insoluble phase containing a gallium-N-organohydroxamic acid chelate which forms from N-organohydroxamic acid and gallium from an aqueous phase containing acids of arsenic.

40. The method of claim 39 wherein an organic solvent is also present to provide an organic phase containing N-organohydroxamic acid and into which the gallium-N-organohydroxamic acid chelate is extracted.

41. The method of effecting oxidation of gallium arsenide which comprises contacting gallium arsenide with an oxidizing agent and a phosphorus complexing agent wherein the phosphorus complexing agent is selected from the group consisting of polybasic phosphates and compounds having two or more organophosphonate groups.

42. The method of claim 41 wherein the complexing agent is 1,2-ethane diphosphonic acid.

43. The method of claim 41 wherein the complexing agent is $Na_3PO_4$ or $K_3PO_4$.

44. The method of claim 41 wherein the complexing agent is $CH_3C(OH)(PO_3H_2)_2$.

45. The method of separating gallium from a gallium arsenide compound which comprises oxidizing the gallium arsenide in the presence of water and a complexing agent to form a gallium-complexing agent complex, and extracting the gallium from the resulting aqueous solution with an N-organohydroxamic acid.

46. The method of claim 45 wherein the complexing agent is an alkali metal tripolyphosphate.

47. The method of claim 45 in which the complexing agent is the compound:

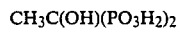

$$CH_3C(OH)(PO_3H_2)_2$$

48. The method of claim 45 wherein the complexing agent is selected from polybasic phosphate complexing or chelating agents, compounds having two or more alkanephosphonate groups, and complexing agents having two or more carboxyl groups.

49. The method of recovering gallium from gallium arsenide which comprises oxidizing the gallium arsenide with an oxidizing agent in the presence of a water insoluble straight chain non-N-substituted hydroxamic acid dissolved in a water immiscible polar solvent to convert the arsenide to an oxide of arsenic and to form a gallium-non-N-substituted hydroxamic acid complex with the straight chain non-N-substituted hydroxamic acid and separating the resulting gasllium-non-N-substituted hydroxamic acid complex from the aqueous medium containing the arsenic compounds.

* * * * *

UNITED STATES PATENT AND TRADEMARK OFFICE
CERTIFICATE OF CORRECTION

PATENT NO. : 4,759,917
DATED : July 26, 1988
INVENTOR(S) : J. P. Coleman et al.

It is certified that error appears in the above—identified patent and that said Letters Patent is hereby corrected as shown below:

In column 3, line 64, delete
"$GaAs+3H_2O_2+\overline{3HA}\not{\longrightarrow}\overline{GaA_3}+H_3AsO_3+3H_2O$" and insert
--$GaAs+3H_2O_2+\overline{3HA}\longrightarrow\overline{GaA_3}+H_3AsO_3+3H_2O$--.

In column 4, line 1, delete
"$GaAs+3H_2O_2+\overline{3HA}\not{\longrightarrow}\overline{GaA_3}+H_3AsO_3+3H_2O$" and insert
--$GaAs+3H_2O_2+\overline{3HA}\longrightarrow\overline{GaA_3}+H_3AsO_3+3H_2O$--.

In column 13, line 22, delete "R" and insert therefor --$R_1$--.

In column 14, line 27, delete "diphosphonio" and insert therefor --diphosphonic--.

In column 15, line 10, delete "metel" and insert therefor --metal--.

In column 19, after the last word in the column insert --separate organic phase, e.g. in Test A with an HA, the amount reported was in the organic solution.--

In column 21, line 2, delete "pheolic" and insert therefor --phenolic--.

In column 22, line 57, delete "oxdiants" and insert therefor --oxidants--.

UNITED STATES PATENT AND TRADEMARK OFFICE
CERTIFICATE OF CORRECTION

PATENT NO. : 4,759,917

DATED : July 26, 1988

INVENTOR(S) : J. P. Coleman et al.

It is certified that error appears in the above—identified patent and that said Letters Patent is hereby corrected as shown below:

In column 23, line 22, delete "coparing" and insert therefor --comparing--.

In column 23, line 48, after the word "The" insert -- complexing agent still serves a function in that it--

In column 24, line 33, after "remaining" insert --in--.

In column 24, line 42, delete "as" and insert therefor --has--.

In column 25, line 32, after "(OH)" insert --(--.

Signed and Sealed this

Twenty-fourth Day of October, 1989

Attest:

DONALD J. QUIGG

*Attesting Officer*  *Commissioner of Patents and Trademarks*